United States Patent [19]
Trah

[11] Patent Number: 5,376,677
[45] Date of Patent: Dec. 27, 1994

[54] BENZO[B]THIOPHENE DERIVATIVES

[75] Inventor: Stephan Trah, Erlenweg, Germany

[73] Assignee: Ciba-Geigy Corporation, Ardsley, N.Y.

[21] Appl. No.: 35,485

[22] Filed: Mar. 22, 1993

Related U.S. Application Data

[60] Continuation of Ser. No. 802,742, Dec. 5, 1991, abandoned, which is a division of Ser. No. 625,765, Dec. 13, 1990, abandoned.

[30] Foreign Application Priority Data

Dec. 14, 1989 [CH] Switzerland .................. 4499/89-6

[51] Int. Cl.$^5$ .................. C07D 333/56; A61K 31/78
[52] U.S. Cl. .................. 514/443; 514/370; 514/337; 514/372; 514/324; 514/233.5; 548/197; 548/214; 549/57; 549/58; 549/59; 546/202; 546/274; 544/145
[58] Field of Search .................. 548/197, 214; 549/57, 549/58, 59; 546/274, 702; 544/145; 514/370, 337, 443, 372, 324, 233.5

[56] References Cited

U.S. PATENT DOCUMENTS 4,816,476 3/1989 Klaus et al. .................. 514/443

FOREIGN PATENT DOCUMENTS 0243014 10/1987 European Pat. Off. .
0342459 11/1989 European Pat. Off. .

OTHER PUBLICATIONS

Schultz et al., Chemical Abstracts, vol. 112 (1990), Abstract No. 216453d.
Schultz et al., Chemical Abstracts, vol. 113 (1990), Abstract No. 152433h.
Beautement et al., Chemical Abstracts, vol. 111 (1989) Abstract No. 114868e.
Clough et al., Chemical Abstracts, vol. 107 (1987) Abstract No. 6939n.
Clough et al., Chemical Abstracts, vol. 109 (1988), Abstract No. 50255b.
Nannini et al., Chemical Abstracts, vol. 96 (1982) Abstract No. 68717b.

*Primary Examiner*—Jane T. Fan
*Attorney, Agent, or Firm*—Wenderoth, Lind & Ponack

[57] ABSTRACT

The invention relates to novel compounds of the formula

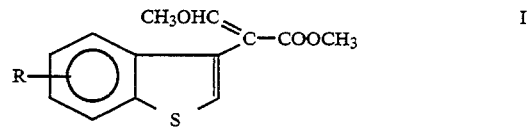

in which R is as defined in the description, to their preparation, to fungicidal compositions which contain such compounds as active substances, and to the use of the active substances or compositions for controlling fungi in agriculture and horticulture.

18 Claims, No Drawings

BENZO[B]THIOPHENE DERIVATIVES

This application is a continuation of now abandoned application Ser. No. 07/802,742, filed Dec. 5, 1991, now abandoned, which is a division of now abandoned application Ser. No. 07/625,765, filed Dec. 13, 1990, now abandoned.

The present invention relates to heterocyclic compounds, namely to benzo[b]thiophene derivatives of the general formula

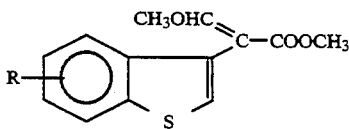

in which $R$ is halogen, $C_{1-4}$alkyl, $C_{1-4}$haloalkyl, $C_{1-4}$alkoxy-$C_{1-4}$alkyl, aryl-$C_{1-4}$alkoxy-$C_{1-4}$alkyl, aryloxy-$C_{1-4}$alkyl, heteroaryloxy-$C_{1-4}$alkyl, arylthio-$C_{1-4}$alkyl, heteroarylthio-$C_{1-4}$alkyl, $C_{2-5}$alkanoyloxy-$C_{1-4}$alkyl (optionally $C_{1-4}$alkyl-substituted $C_{3-6}$cycloalkyl)-carbonyloxy-$C_{1-4}$alkyl, aroyloxy-$C_{1-4}$alkyl, aryl-$C_{2-5}$alkanoyloxy-$C_{1-4}$alkyl, heteroaryl-$C_{2-5}$alkanoyloxy-$C_{1-4}$alkyl, $C_{1-4}$alkoxy, aryloxy or one of the groups (a) to (e)

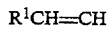 (a)

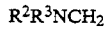 (b)

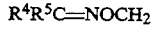 (c)

 (d)

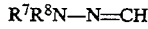 (e), $R^1$ is aryl or heteroaryl, $R^2$ and $R^3$ independently of one another are hydrogen, $C_{1-4}$alkyl, aryl-$C_{1-4}$alkyl, aryl or heteroaryl or $R^2$ and $R^3$ together with the nitrogen atom to which they are bonded are a 5- or 6-membered ring which may contain an oxygen or sulfur atom, $R^4$ and $R^5$ independently of one another are hydrogen, $C_{1-4}$alkyl, $C_{1-4}$haloalkyl, $C_{1-4}$alkoxy-$C_{1-4}$alkyl, $C_{1-4}$alkylthio-$C_{1-4}$alkyl, aryl-$C_{1-4}$alkyl, $C_{3-6}$cycloalkyl, aryl, heteroaryl, $C_{1-4}$alkoxy or aroyl, or $R^4$ and, $R^5$ together with the carbon atom to which they are bonded are a 5- or 6-membered carbocyclic or heterocyclic ring to which one or two benzene rings may be fused, $R^6$ is aryl, heteroaryl, $C_{1-4}$alkoxy, aryl-$C_{1-4}$alkoxy or $C_{3-4}$alkenyloxy, and $R^7$ and $R^8$ independently of one another are hydrogen, $C_{1-4}$alkyl, aryl, heteroaryl or arylsulfonyl.

The compounds according to the invention have fungicidal properties and are suitable as fungicidal active substances, in particular for use in agriculture and in horticulture.

The invention furthermore relates to a process for the preparation of the compounds according to the invention, to fungicidal compositions which contain such compounds as active substances, and to the use of such compounds and compositions for controlling fungi in agriculture and in horticulture.

In the above formula I, all "alkyl" groups, as such or as part of larger groups, such as heteroarylalkyl, can be straight-chain or branched, depending on the number of their carbon atoms. A halogen atom which may be present is fluorine, chlorine, bromine or iodine, fluorine, chlorine and bromine being preferred. A haloalkyl group can have one or more halogen substituents which can be identical or different. Aryl is understood as meaning, in particular, phenyl or naphthyl, heteroaryl is understood as meaning a heterocyclic group which has aromatic character, for example pyridyl, furyl, thienyl, isoxazolyl, thiazolyl, imidazolyl, pyrimidinyl or 1,3,4-thiadiazolyl, or such a group to which benzene is fused, for example, benzoxazolyl. This is also true for aryl or heteroaryl as part of a larger group, for example aralkyl or heteroarylalkyl. Each of the aryl and heteroaryl groups can have one or more substituents, advantageously selected from amongst halogen, $C_{1-4}$alkyl, $C_{1-4}$haloalkyl, $C_{1-4}$alkylthio-$C_{1-4}$alkyl, $C_{1-4}$alkoxy, $C_{1-4}$haloalkoxy, aryl-$C_{1-4}$alkoxy, $C_{3-6}$alkenyloxy, aryloxy, $C_{1-4}$alkylthio, $C_{3-6}$cycloalkyl-$C_{1-4}$alkylthio, nitro and tri($C_{1-4}$alkyl)silyl. Moreover, a tetrahydrofuran, dioxolane or dioxane ring can be fused to a phenyl group, so that the corresponding group is 2,3-dihydrobenzofuranyl, 1,3-benzodioxolanyl or 1,4-benzodioxanyl. The 5- or 6-membered heterocyclic ring $R^2R^3N$ [part of group (b)] can also be substituted, in particular by one or more $C_{1-4}$alkyl groups.

The substituent R is in each case in the 4-, 5-, 6- of 7-position of the benzo[b]thiophene ring, the 5-position being preferred.

If the compounds of the formula I contain asymmetric carbon atoms, the compounds occur in optically active form. On the basis of the presence of the aliphatic double bond alone, the compounds occur in the [E] or [Z] form in any case. Atropo-isomery can also occur. The formula I is intended to embrace all these possible isomeric forms, and their mixtures, for example racemic mixtures and any [E/Z] mixtures.

A particular sub-group of the compounds of the formula I consists of those compounds I in which R is halogen, $C_{1-4}$alkyl, $C_{1-4}$haloalkyl, $C_{1-4}$alkoxy-$C_{1-4}$alkyl, aryloxy-$C_{1-4}$alkyl, heteroaryloxy-$C_{1-4}$alkyl, arylthio-$C_{1-4}$alkyl, heteroarylthio-$C_{1-4}$alkyl, $C_{1-4}$alkoxy, aryloxy or one of the abovementioned groups (a) to (d), $R^1$, $R^2$ and $R^3$ are as defined above, and $R^4$ and $R^5$ independently of one another are hydrogen, $C_{1-4}$alkyl, $C_{1-4}$haloalkyl, $C_{1-4}$alkoxy-$C_{1-4}$alkyl, $C_{3-6}$cycloalkyl, aryl or heteroaryl, and $R^6$ is aryl or heteroaryl.

Particularly preferred individual compounds of the formula I are:

Methyl α{5-(α-methyl-m-trifluoromethylbenzylideneaminooxymethyl)-3-benzo[b]thienyl}-β-methoxyacrylate, methylα-{5-(α-[n-propyl]-benzylideneaminooxymethyl)-3-benzo[b]thienyl}-β-methoxyacrylate, methyl α-{5-[α-(2-pyridyl)-ethylideneaminooxymethyl]-3-benzo[b]thienyl}-β-methoxyacrylate, methyl α-{5-(α-cyclopropyl-4-chlorobenzylideneaminooxymethyl)-3-benzo[b]thienyl}-β-methoxyacrylate, methyl α-{5-methoxy-3-benzo[b]thienyl}-β-methoxyacrylate, methyl α-{5-ethoxy-3-benzo[b]thienyl}-β-methoxyacrylate, methyl α-{5-[(α-phenylethyl)methylaminomethyl]-3-benzo[b]thienyl}-β-methoxyacrylate, methyl α-{5-(dicyclopropylmethylideneaminooxymethyl)-3-benzo[b]thienyl}-β-methoxyacrylate,
methyl α-{5-[(cyclopropyl)(2-pyridyl)methylideneaminooxymethyl]-3-benzo[b]thienyl}-β-methoxyacrylate,
methyl α-{5-(α-cyclopropyl-m-trifluoromethylbenzylideneaminooxymethyl)-3-benzo[b]thienyl}-β-methoxyacrylate,
methyl α-{5-(α-cyclopropylbenzylideneaminooxymethyl)-3-benzo[b]thienyl}-β-methoxyacrylate,
methyl α-{5-[β-methyl-α-(2-pyridyl)propylideneaminooxymethyl]-3-benzo[b]thienyl}-β-methoxyacrylate and
methyl α-{5-(2-isopropyl-4-methyl-2,5-dihydrothiazol-5-ylideneaminooxymethyl)-3-benzo[b]thienyl}-β-methoxyacrylate.

The process according to the invention for the preparation of the compounds of the general formula I comprises
a) to prepare those compounds of the formula I in which R is other than a group (b), (c), (d) or (e), treating a methyl α-(3-benzo[b]thienyl)-β-hydroxyacrylate of the general formula

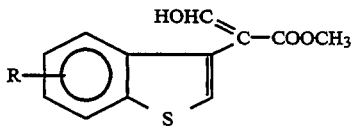

in which R is as defined above, with the exception of a group (b), (c), (d) or (e), with a methylating agent,
b) to prepare those compounds of the formula I in which R is bromomethyl, treating a methyl α-(methyl-3-benzo[b]thienyl)-β-methoxyacrylate of the general formula

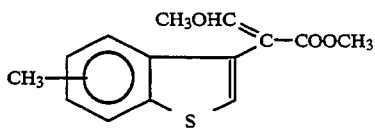

with N-bromosuccinimide,
c) to prepare those compounds of the formula I in which R is $C_{1-4}$alkoxymethyl, aryl-$C_{1-4}$alkoxymethyl, aryloxymethyl, heteroaryloxymethyl, arylthiomethyl, heteroarylthiomethyl, $C_{1-5}$alkanoyloxymethyl, (optionally $C_{1-4}$alkyl-substituted $C_{1-6}$cycloalkyl)carbonyloxymethyl, aroyloxymethyl, aryl-$C_{2-5}$alkanoyloxymethyl, heteroaryl-$C_{2-5}$alkanoyloxymethyl, a group (b) or a group (c), reacting a methyl α-(bromomethyl-3-benzo[b]thienyl)-β-methoxyacrylate of the general formula

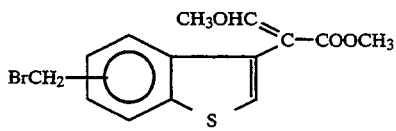

with a hydroxy compound, a mercapto compound, a carboxylic acid, an amine or an oxime of the general formula

R'—H    III in which R' is $C_{1-4}$alkoxy, aryl-$C_{1-4}$alkoxy, aryloxy, heteroaryloxy, $C_{1-5}$alkanoyloxy, (optionally $C_{1-4}$alkyl-substituted $C_{3-6}$cycloalkyl)carbonyloxy, aroyloxy, aryl-$C_{2-5}$alkanoyloxy, heteroaryl-$C_{2-5}$alkanoyloxy, arylthio, heteroarylthio, a group $R^2R^3N$ (b') or a group $R^4R^5C=NO$ (c'),
d) to prepare those compounds of the formula I in which R is a group (a), reacting a dialkyl {3-(α-methoxycarbonyl-β-methoxyvinyl)-benzo[b]thienyl} methylphosphonate of the general formula

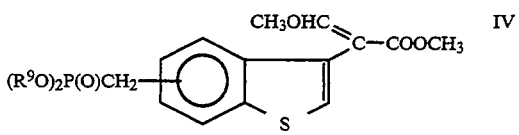

in which $R^9$ is $C_{1-4}$alkyl
with an aldehyde of the general formula $R^1$CHO    V in which $R^1$ has the abovementioned meaning, or
e) to prepare those compounds of the formula I in which R is a group (d) or a group (e), reacting a methyl α-(formyl-3-benzo[b]thienyl)-β-methoxyacrylate of the general formula

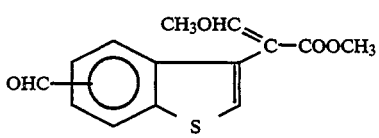

with an amine, hydroxylamine or hydrazine of the general formula $R^6$NH$_2$    VII or $R^7R^8$N—NH$_2$    VIII in which $R^6$, $R^7$ and $R^8$ are as defined above.

Process variant a) is the methylation of the β-hydroxy substituent of the acrylic acid derivative II. This methylation step can be carried out under the reaction conditions customary for such cases. The reaction is expediently carried out in an inert organic solvent such as acetone, dimethylformamide or dimethyl sulfoxide, in the presence of a base such as sodium hydride or of an alkali metal carbonate, for example sodium carbonate or potassium carbonate, at temperatures between 20° C. and 80° C., preferably in the temperature range from 40° C. to 60° C.

The bromination as in process variant b) can also be carried out in a manner known per se, namely expediently in an inert organic solvent such as halogenated hydrocarbon, for example carbon tetrachloride, in the presence of a radical-forming initiator, for example azoisobutyronitrile or dibenzoyl peroxide, at temperatures between 70° C. and 90° C., preferably at about 80° C. An example of such a bromination is described by Homer et at. in Angew. Chem. 71, 349–365 (1959).

The reaction as in process variant c) represents a nucleophilic substitution which is advantageously effected in an inert organic solvent such as an aliphatic or cyclic ether, for example dimethoxyethane, tetrahydrofuran or dioxane; an aliphatic ketone, for example acetone; dimethylformamide or dimethyl sulfoxide, in the presence of a base such as sodium hydride, of an alkali metal carbonate, for example sodium carbonate or potassium carbonate, or a tertiary amine, for example a trialkylamine, in particular diazabicyclononane or diazabicycloundecane, or silver oxide, at temperatures between 0° C. and 100° C., preferably in the temperature range from 20° C. to 80° C.

The reaction as in process variant d) is a Wittig-Homer reaction which is expediently carried out in an inert organic solvent such as an aliphatic or cyclic ether, for example 1,2-dimethoxyethane or tetrahydrofuran, in the presence of a base, for example sodium hydride, at temperatures between 20° C. and 80° C. Examples of such a reaction can be found in J.A.C.S. 83, 1733–1738 (1961) (Wadsworth et al.).

The condensation as in process variant e) can be carried out in a manner known per se, namely expediently in an organic solvent such as an alkanol, for example methanol or ethanol, tetrahydrofuran or pyridine, if appropriate with the addition of a catalytic amount of p-toluene sulfonic acid, at temperatures between 20° C. and 110° C.

The compounds of the formula I which have been prepared in this manner can be isolated and purified by customary methods. Any mixtures of isomers obtained, for example E/Z isomer mixtures, can likewise be separated into the pure isomers by customers methods, for example by chromatography or fractional crystallization.

The methyl α-(3-benzo[b]thienyl)-β-hydroxyacrylates of the formula II which are used as starting materials in process variant a) can be prepared in a manner known per se, for example as in the following equation:

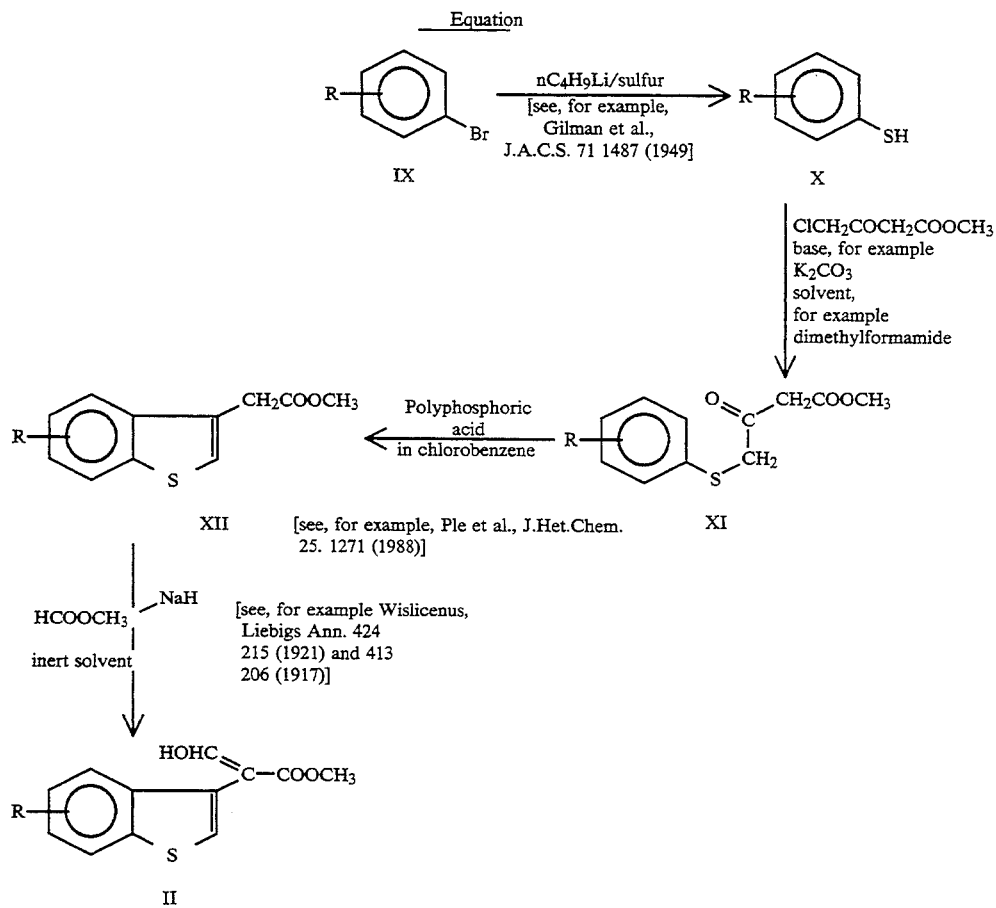

The dialkyl {3-(α-methoxycarbonyl-β-methoxyvinyl)benzo[b]thienyl}methylphosphonates of the formula IV which are used as starting materials in process variant d) can be prepared in a manner known per se by reacting the corresponding methyl α-(bromomethyl-3-benzo[b]thienyl)-β-methoxyacrylate of the abovementioned formula Ib with a trialkyl ester of phosphorous acid [see, for example, Houben-Weyl, Methoden der organischen Chemie (Methods in Organic Chemistry), Vol. 12/I, 433 et seq. (1963)].

The methyl α-(formyl-3-benzo[b]thienyl)-β-methoxyacrylates of the formula VI which are used as starting materials in process variant e) can also be prepared in a manner known per se, namely by reacting the corresponding methyl α-(bromomethyl-3-benzo[b]thienyl)-β-methoxyacrylate of the abovementioned formula Ib with sodium hydrogen carbonate and dimethyl sulfoxide [the Kornblum reaction, see, for example, J.A.C.S. 79, 6562 et seq. (1957)].

The methyl α-(methyl-3-benzo[b]thienyl)-β-methoxyacrylates of the formula Ia which are used as starting materials in process variant b), and the methyl α-(bromomethyl-3-benzo[b]thienyl)-β-methoxyacrylates of the formula Ib which are used as starting materials in process variant c) are sub-groups of the compounds of the formula I, which can be prepared, for example, by process variant a) or b). The starting materials of the formulae III, V, VII, VIII and IX are either known or can be prepared by methods known per se.

The compounds according to the invention have a fungicidal action and can accordingly be used for controlling fungi in agriculture, in horticulture and in wood processing. They are particularly suitable for inhibiting the growth or for destroying phytopathogenic fungi on parts of plants, for example leaves, stalks, roots, tubers, fruits or flowers and on seeds, and also harmful fungi which occur in the soil. It is furthermore possible to control wood-destroying and wood-discolouring fungi with the compounds according to the invention. The compounds according to the invention are active, for example, for controlling of fungi of the classes of the Deuteromycetes, Ascomycetes, Basidiomycetes and Phycomycetes.

The compounds according to the invention are particularly suitable for controlling the following pathogens:

Powdery mildews (for example *Erysiphe graminis, Erysiphe cichoracearum, Podosphaera leucotricha, Uncinula necator, Sphaerotheca spp.*)

Rusts (for example *Puccinia tritici, Puccinia recondita, Puccinia hordei, Puccinia coronata, Puccinia striiformis, Puccinia arachidis, Hemileia vastatrix, Uromyces fabae*)

Scabs (for example *Venturia inaequalis*)

Cercospora spp. (for example *Cercospora arachidicola, Cercospora beticola*)

Mycosphaerella spp. (for example *Mycosphaerella fijiensis*)

Alternaria spp. (for example *Alternaria brassicae, Alternaria mali*)

Septoria spp. (for example *Septoria nodorum*)

Heminthosporium spp. (for example *Helminthosporium teres, Helminthosporium oryzae*)

Plasmopara spp. (for example *Plasmopara viticola*)

Pseudoperonospora spp. (for example *Pseudoperonospora cubensis*)

Phytophtora spp. (for example *Phytophtora infestans*)

Pseudocercosporella spp. (for example *Pseudocercosporella herpotrichoides*)

Pyricularia spp. (for example *Pyricularia oryzae*).

The compounds are furthermore active for example against fungi of the genera Tilletia, Ustilago, Rhizoctonia, Verticillium, Fusarium, Pythium, Gaeumannomyces, Sclerotinia, Monilia, Botrytis, Peronospora, Bremia, Gloeosporium, Cercosporidium, Penicillium, Ceratocystis, Rhynchosporium, Pyrenophora, Diaporthe, Ramularia and Leptosphaeria. Certain representatives of the compounds according to the invention also have an action against wood-destroying fungi, for example of the genera Coniophora, Gloeophyllum, Poria, Merulius, Trametes, Aureobasidium, Sclerophoma and Trichoderma.

The compounds according to the invention are distinguished by a prophylactic and curative action.

The compounds according to the invention are active against phytopathogenic fungi under greenhouse conditions at concentrations of as little as 0.5 mg up to 500 mg of active substance per liter of spray liquor. In the open, it is advantageous to use dosage rates from 20 g to 1 kg of active substance of the formula I per hectare per treatment. To control seed- or soil-borne fungi by seed dressing, it is advantageous to use dosage rates from 0.01 g to 1.0 g of active substance of the formula I per kg of seed.

The compounds according to the invention can be formulated to give various compositions, for example solutions, suspensions, emulsions, emulsifiable concentrates and preparations in the form of powders. The fungicidal compositions according to the invention comprise an effective amount of at least one compound of the general formula I as defined above, and formulation auxiliaries. The compositions expediently contain at least one of the following formulation auxiliaries:

Solid carriers; solvents or dispersants; surfactants (wetting agents and emulsifiers); dispersing agents (without surfactant action); and stabilizers.

Suitable solid carriers are mainly: natural minerals, such as kaolin, clays, kieselguhr, talc, bentonite, chalk, for example whiting, magnesium carbonate, limestone, quartz, dolomite, attapulgite, montmorillonite and diatomaceous earth; synthetic minerals, such as highly-disperse silica, aluminium oxide and silicates; organic substances such as cellulose, starch, urea and synthetic resins; and fertilizers, such as phosphates and nitrates, it being possible for such carriers to be, for example, in granule or powder form.

Suitable solvents or dispersants are mainly: aromatics, such as toluene, xylenes, benzene and alkylnaphthalines; chlorinated aromatics and chlorinated aliphatic hydrocarbons, such as chlorobenzenes, chloroethylenes and methylene chloride; aliphatic hydrocarbons such as cyclohexane and paraffins, for example petroleum fractions; alcohols such as butanol and glycol as well as their ethers and esters; ketones such as acetone, methyl ethyl ketone, methyl isobutyl ketone and cyclohexanones; and strongly polar solvents and dispersing agents such as dimethylformamide, N-methylpyrrolidone and dimethyl sulfoxide, such solvents or dispersing agents preferably having flashpoints of at least 30° C. and boiling points of at least 50° C., and water. From amongst the solvents and dispersing agents, so-called liquified gaseous extenders or carriers are also suitable, which are products which are gaseous at room temperature and under atmospheric pressure. Examples of such products, are in particular, aerosol propellants such as halohydrocarbons, for example dichlorodifluoromethane. In the event that water is used as the solvent, for example organic solvents can also be used as auxiliary solvents.

The surfactants (wetting agents and emulsifiers) can be non-ionic compounds such as condensation products of fatty acids, fatty alcohols or fat-substituted phenols with ethylene oxide; fatty acid esters and fatty acid ethers of sugars or of polyhydric alcohols; the products which are obtained from sugars or polyhydric alcohols by condensation with ethylene oxide; block polymers of ethylene oxide and propylene oxide; or alkyldimethylamine oxides.

The surfactants can also represent anionic compounds such as soaps; fatty sulfate esters, for example dodecyl sodium sulfate, octadecyl sodium sulfate and cetyl sodium sulfate; alkylsulfonates, arylsulfonates and fatty-aromatic sulfonates such as alkylbenzenesulfonates, for example calcium dodecylbenzenesulfonate, and butylnaphthalenesulfonates; and more complex fatty sulfonates, for example the amide condensation products of oleic acid and N-methyltaurine, and the sodium sulfonate of dioctyl succinate.

Finally, the surfactants can be cationic compounds such as alkyldimethylbenzylammonium chlorides, dialkyldimethylammonium chlorides, alkyltrimethylammonium chlorides and ethoxylated quaternary ammonium chlorides.

The following are mainly suitable as dispersants (without surfactant action): lignin, sodium salts and ammonium salts of lignin sulfonic acid, sodium salts of maleic anhydride/diisobutylene copolymers, sodium salts and ammonium salts of sulfonated polycondensation products of naphthalene and formaldehyde, and sulfite waste liquors.

The following are examples which can be employed as dispersants which are particularly suitable as thickeners or anti-settling agents: methylcellulose, carboxymethylcellulose, hydroxyethylcellulose, polyvinyl alcohol, alginates, caseinales and blood albumin.

Examples of suitable stabilizers are acid-binding agents, for example epichlorohydrin, phenyl glycidyl ether and soya epoxides; antioxidants, for example gallic acid esters and butylhydroxytoluene; UV absorbers, for example substituted benzophenones, diphenylacrylonitrilic acid esters and cinnamic acid esters; and deactivators, for example salts of ethylenediaminetetraacetic acid, and polyglycols.

Besides the active substances of the formula I, the fungicidal compositions according to the invention can also contain other active substances, for example other fungicidal compositions, insecticidal and acaricidal compositions, bactericides, plant-growth regulators and fertilizers. Such combined preparations are suitable for widening the spectrum of action or for specifically influencing plant growth.

In general, the fungicidal compositions according to the invention contain between 0.0001 and 85 percent by weight of compound according to the invention, or compounds according to the invention, as the active substance(s), depending on the nature of these compositions. They can be in a form which is suitable for storage and transport. In such forms, for example emulsifiable concentrates, the active substance concentration is usually in the upper range of the above concentration interval. These forms can then be diluted with identical or different formulation auxiliaries down to active substance concentrations which are suitable for use in practice, and such concentrations are usually in the lower range of the above concentration interval. Emulsifiable concentrates generally contain 5 to 85 percent by weight, preferably 25 to 75 percent by weight, of the compound(s) according to the invention. Suitable use forms are, inter alia, ready-for-use solutions, emulsions and suspensions which are suitable, for example, as spray liquors. Such spray liquors can contain concentrations of between, for example, 0.0001 and 20 percent by weight. Using the ultra-low-volume method, it is possible to formulate spray liquors in which the active substance concentration is preferably from 0.5 to 20 percent by weight, while the spray liquors formulated using the low-volume method and the high-volume method preferably have an active substance concentration of 0.02 to 1.0, or 0.002 to 0.1, percent by weight.

The fungidical compositions according to the invention can be prepared by mixing at least one compound according to the invention with formulation auxiliaries.

The compositions can be prepared in a known manner, for example by mixing the active substance with solid carriers, by dissolving or suspending them in suitable solvents or dispersing agents, if appropriate with the use of surfactants as wetting agents or emulsifiers or of dispersants, by diluting pre-prepared emulsifiable concentrates with solvents or dispersing agents, etc.

In the case of compositions in the form of powders, the active substance can be mixed with a solid carrier, for example by jointly grinding them; or the solid carrier can be impregnated with a solution or suspension of the active substance and the solvent or dispersing agent can then be removed by evaporation, heating or by filtering off under reduced pressure. By adding surfactants or dispersants, such compositions in the form of powders can be rendered readily wettable with water, so that they can be converted into aqueous suspensions which are suitable, for example, as spray liquors.

The compounds according to the invention can also be mixed with a surfactant and a solid carrier to form a wettable powder which is dispersible in water, or they can be mixed with a solid pregranulated carrier to form a granular product.

If desired, a compound according to the invention can be dissolved in a solvent which is not miscible with water such as, for example, an alicyclic ketone, which expediently contains dissolved emulsifier, so that the solution has a self-emulsifying effect when water is added. On the other hand, the active substance can be mixed with an emulsifier and the mixture can then be diluted with water to the desired concentration. Moreover, the active substance can be dissolved in a solvent and the solution can then be mixed with an emulsifier. Such a mixture can likewise be diluted with water to the desired concentration. In this manner, emulsifiable concentrates or ready-for-use emulsions are obtained.

The compositions according to the invention can be used following the application methods customary in plant protection or in agriculture. The method according to the invention for controlling fungi comprises treating the goods to be protected, for example plants, parts of plants, or seeds, with an effective amount of a compound according to the invention or of a composition according to the invention.

The examples below illustrate the invention.

I. Preparation of the active substances of the formula I:

EXAMPLE 1

A solution of 79.7 g of methyl 5-methyl-3-benzo[b]thienylacetate in 200 ml of dimethylformamide and 200 ml of methyl formate is slowly added dropwise to a suspension of 10.4 g of sodium hydride in 100 ml of dimethylformamide. The reaction mixture is stirred for 2 hours at room temperature and then acidified with dilute hydrochloric acid, and this is then extracted with ethyl acetate. The organic phase is washed with water, dried over anhydrous sodium sulfate and concentrated under reduced pressure. In this manner, methyl $\alpha$-(5-methyl-3-benzo[b]thienyl)-$\beta$-hydroxyacrylate is obtained as the crude product which is used unpurified as the starting material in the next process step.

The above starting material together with 36 ml of dimethyl sulfate, 69 g of potassium carbonate and 315 ml of acetone is refluxed for 2 hours. The mixture is cooled to room temperature and filtered, and the filtrate is concentrated under reduced pressure and thus gives a yellow oil. This oil is purified by chromatography on silica gel using diethyl ether/n-hexane (1:1). The crude product is recrystallized from methylene chloride/n-hexane, which gives methyl $\alpha$-(5-methyl-3-benzo[b]thienyl)-$\beta$-methoxyacrylate as yellow crystals, m.p. 11420 –115° C.

EXAMPLES 2-10

Analogously to the process described in Example 1, the substituted methyl 3-benzo[b]thienylacetate in question is reacted with methyl formate to give the corresponding methyl α-(3-benzo[b]thienyl)-β-hydroxyacrylate, and the latter is subsequently methylated using dimethyl sulfate to prepare the compounds of the formula I listed in Table 1 below:

TABLE 1

[Structure: R-substituted benzo[b]thiophene with CH3OHC=C-COOCH3 group, positions 4,5,6,7 on benzene ring and S in thiophene ring]

| Example | R | Physical data |
|---|---|---|
| 2 | 7-methyl | m.p. 89–90° C. |
| 3 | 5-tert-butyl | [E] isomer: oil |
|   |   | [Z] isomer: oil |
| 4 | 5-methoxy | m.p. 112–113° C. |
| 5 | 7-methoxy | m.p. 115–116° C. |
| 6 | 6-methoxy | m.p. 127–128° C. |
| 7 | 5-bromo | m.p. 136–137° C. |
| 8 | 5-chloro | m.p. 119° C. |
| 9 | 5-ethoxy | m.p. 130° C. |
| 10 | 5-phenoxy | oil |

EXAMPLE 11

A mixture of 71 g of methyl α-(5-methyl-3-benzo[b]-thienyl)-β-methoxyacrylate (see Example 1), 57.8 g of N-bromosuccinimide, 1.1 g of azodiisobutyronitrile and 720 ml of carbon tetrachloride is refluxed for 75 minutes. The mixture is cooled to room temperature and filtered, and the filtrate is then concentrated under reduced pressure, and the yellow oil which remains is purified by chromatography on silica gel using diethyl ether/n-hexane (1:1). The crude product is crystallized from methylene chloride/n-hexane, and methyl α-(5-bromomethyl-3-benzo[b]thienyl)-β-methoxyacrylate is obtained in this manner as pale yellow crystals, m.p. 124°–125° C.

EXAMPLE 12

Analogously to the process described in Example 11, methyl α-(7-methyl-3-benzo[b]thienyl)-β-methoxyacrylate (see Example 2) is brominated with N-bromosuccinimide to give methyl α-(7-bromomethyl-3-benzo[b]-thienyl-β-methoxyacrylate, m.p. 97° C.

EXAMPLE 13

A mixture of 1 g of methyl α-(5-bromomethyl-3-benzo[b]-thienyl)-β-methoxyacrylate (see Example 11), 0.28 g of phenol and 2 g of potassium carbonate in 20 ml of dimethylformamide is heated for 2 hours at 50° C. The mixture is cooled to room temperature and filtered, and the filtrate is then concentrated under reduced pressure, and the crude product is purified by chromatography on silica gel using diethyl ether/n-hexane (1:1). Recrystallization from methylene chloride/n-hexane gives methyl α-(5-phenoxymethyl-3-benzo[b]-thienyl)-β-methoxyacrylate as colourless crystals, m.p. 130° C.

EXAMPLES 14–55

Analogously to the process described in Example 13, methyl α-(5-bromomethyl-3-benzo[b]thienyl)-β-methoxyacrylate is reacted with the hydroxy or mercapto compound, the carboxylic acid or the amine in question, of the formula HI, to prepare the compounds of the formula I listed in Table 2 below:

TABLE 2

[Structure: R-substituted benzo[b]thiophene with CH3OHC=C-COOCH3 group]

| Example | R | Physical data |
|---|---|---|
| 14 | 5-[(5-methyl-3-isoxazolyl)-oxymethyl] | m.p. 127° C. |
| 15 | 5-(3-nitrophenoxymethyl) | m.p. 128° C. |
| 16 | 5-(3-fluorophenoxymethyl) | m.p. 109–110° C. |
| 17 | 5-(α,α,α-trifluoro-m-tolyloxymethyl) | m.p. 83° C. |
| 18 | 5-(3-chlorophenoxymethyl) | m.p. 111–112° C. |
| 19 | 5-(4-chlorophenoxymethyl) | m.p. 141° C. |
| 20 | 5-(m-tolyloxymethyl) | m.p. 131–132° C. |
| 21 | 5-(p-tolyloxymethyl) | m.p. 142–143° C. |
| 22 | 5-(3-ethylphenoxymethyl) | m.p. 82° C. |
| 23 | 5-(4-ethylphenoxymethyl) | m.p. 109–110° C. |
| 24 | 5-(4-tert-butyl-phenoxymethyl) | m.p. 124–125° C. |
| 25 | 5-(4-nitro-m-tolyloxymethyl) | m.p. 140–141° C. |
| 26 | 5-(4-chloro-m-tolyloxymethyl) | m.p. 118–119° C. |
| 27 | 5-phenylthiomethyl | m.p. 95–96° C. |
| 28 | 5-[5-(cyclopropylmethyl-thio)-1,3,4-thiadiazol-2-yl-thiomethyl] | oil |
| 29 | 5-(4-chlorophenylthiomethyl) | m.p. 133° C. |
| 30 | 5-(p-tolylthiomethyl) | m.p. 125° C. |
| 31 | 5-(4-tert-butyl-phenylthiomethyl) | m.p. 131–132° C. |
| 32 | 5-(2-benzoxazolylthiomethyl) | m.p. 117–118° C. |
| 33 | 5-piperidinomethyl | m.p. 105–106° C. |
| 34 | 5-(2,6-dimethylmorpholinomethyl) | oil |
| 35 | 5-[(α-phenylethyl)methylaminomethyl] | oil |
| 36 | 5-[(5-methyl-3-isoxazolyl)-methylaminomethyl] | oil |
| 37 | 5-[(1-naphthylmethyl)methylaminomethyl] | oil |
| 38 | 5-(3,4-dimethylphenoxymethyl) | m.p. 134–135° C. |
| 39 | 5-anilinomethyl | m.p. 141–142° C. |
| 40 | 5-(α,α,α-trifluoro-m-tolylaminomethyl) | oil |
| 41 | 5-(3-bromophenoxymethyl) | m.p. 114–115° C. |
| 42 | 5-[(m-tolyl)methylaminomethyl] | oil |
| 43 | 5-(8-quinolinyloxymethyl) | oil |
| 44 | 5-methoxymethyl | oil |
| 45 | 5-(α-methylbenzyloxymethyl) | oil |
| 46 | 5-[(1-methylcyclopropyl)carbonyloxymethyl | oil |
| 47 | 5-(benzylmethylaminomethyl) | oil |
| 48 | 5-(4,6-dimethylpyrimidin-2-ylthiomethyl) | m.p. 118–120° C. |
| 49 | 5-(3-pyridylacetoxymethyl) | m.p. 77–78° C. |
| 50 | 5-(α,α,α-trifluoro-p-tolylacetoxymethyl) | m.p. 105–106° C. |
| 51 | 5-(2,4-dichlorobenzoyloxymethyl) | m.p. 119° C. |
| 52 | 5-cyclopropylcarbonyloxymethyl | oil |
| 53 | 5-(2,4-dichlorophenylacetoxymethyl) | m.p. 99–100° C. |
| 54 | 5-(3-benzo[b]thienyl-acetoxymethyl | oil |
| 55 | 5-(3,4-dichlorophenylacetoxymethyl) | oil |

EXAMPLE 56

To 77 mg of sodium hydride in 20 ml of dimethylformamide there are added 1 g of methyl α-(5-bromomethyl-3-benzo[b]thienyl)-β-methoxyacrylate (see Example 11) and 0.59 g of 3-trifluoromethylacetophenone oxime. After the reaction mixture has been stirred for 15 minutes, saturated sodium hydrogen carbonate solution is added and the mixture is extracted three times using ethyl acetate. The organic phase is dried over anhydrous sodium sulfate and then concentrated. The yellow oil which remains is purified by chromatography on silica gel using diethyl ether/n-hexane (1:1) and recrystallized from diethyl ether/n-hexane. This gives methyl α-[5-(α-methyl-m-trifluoromethylbenzylideneaminooxymethyl)-3-benzo[b]thienyl]-β-methoxyacrylate as colourless crystals, m.p. 110°–111° C.

EXAMPLES 57–184

Analogously to the process described in Example 56, methyl α-(5-bromomethyl-3-benzo[b]thienyl)-β-methoxyacrylate is reacted with the oxime in question, of the formula III, to give the compounds of the formula I listed in Table 3 below:

TABLE 3

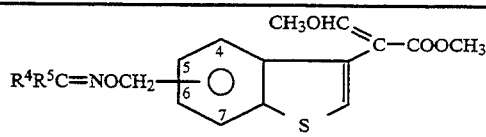

| Example | Position of $R^4R^5C{=}NOCH_2-$ | $R^4$ | $R^5$ | Physical data |
|---|---|---|---|---|
| 57 | 5- | phenyl | trifluoromethyl | oil |
| 58 | 5- | phenyl | methyl | m.p. 123° C. |
| 59 | 5- | 4-chlorophenyl | methyl | m.p. 135–136° C. |
| 60 | 5- | 2-thienyl | methyl | m.p. 111–112° C. |
| 61 | 5- | m-tolyl | hydrogen | m.p. 86–87° C. |
| 62 | 5- | 3-chlorophenyl | methyl | m.p. 121–122° C. |
| 63 | 5- | 3,4-dichlorophenyl | methyl | m.p. 149–150° C. |
| 64 | 5- | 4-nitrophenyl | methyl | m.p. 161° C. |
| 65 | 5- | phenyl | n-propyl | oil |
| 66 | 5- | cyclopropyl | cyclopropyl | oil |
| 67 | 5- | 2-furyl | methyl | m.p. 109° C. |
| 68 | 5- | 2-pyridyl | methyl | m.p. 107–109° C. |
| 69 | 5- | 3-pyridyl | methyl | m.p. 124–125° C. |
| 70 | 5- | 4-chlorophenyl | n-propyl | oil |
| 71 | 5- | 4-chlorophenyl | cyclopropyl | oil |
| 72 | 5- | 3-fluoro-5-trifluoromethyl-phenyl | methyl | m.p. 92–93° C. |
| 73 | 5- | 3,5-difluorophenyl | methyl | m.p. 129–130° C. |
| 74 | 5- | 3-fluorophenyl | methyl | m.p. 129–130° C. |
| 75 | 5- | 3-trifluoromethoxy-phenyl | methyl | m.p. 75–76° C. |
| 76 | 5- | 2,5-dimethyl-3-furyl | methyl | m.p. 78° C. |
| 77 | 5- | 3-thienyl | methyl | m.p. 130–131° C. |
| 78 | 5- | 2-thienyl | cyclopropyl | oil |
| 79 | 5- | 3-methoxyphenyl | methyl | m.p. 99° C. |
| 80 | 5- | 4-tert-butyl-phenyl | methyl | m.p. 95° C. |
| 81 | 5- | 4-difluoromethoxy-phenyl | methyl | m.p. 98° C. |
| 82 | 5- | α,α,α-trifluoro-m-tolyl | trifluoromethyl | oil |
| 83 | 5- | α,α,α-trifluoro-m-tolyl | ethyl | oil |
| 84 | 5- | 3-chlorophenyl | ethyl | m.p. 81–82° C. |
| 85 | 5- | α,α,α-trifluoro-m-tolyl | n-propyl | oil |
| 86 | 5- | α,α,α-trifluoro-m-tolyl | methoxymethyl | m.p. 101–102° C. |
| 87 | 5- | methyl | methyl | m.p. 102–103° C. |
| 88 | 5- | isopropyl | methyl | m.p. 69–70° C. |
| 89 | 5- | 1-methyl-2-pyrrolyl | methyl | m.p. 149° C. |
| 90 | 5- | 2-pyridyl | cyclopropyl | oil |
| 91 | 5- | 2-thiazolyl | cyclopropyl | 1. isomers: m.p. 146–147° C. 2. isomers: m.p. 92–93° C. |
| 92 | 5- | 3-bromophenyl | methyl | m.p. 112° C. |
| 93 | 5- | α,α,α-trifluoro-m-tolyl | cyclopropyl | oil |
| 94 | 5- | 4-fluorophenyl | cyclopropyl | m.p. 97–99° C. |
| 95 | 5- | 4-pyridyl | methyl | m.p. 159–160° C. |
| 96 | 5- | phenyl | cyclopropyl | oil |
| 97 | 5- | 3-chlorophenyl | cyclopropyl | oil |
| 98 | 5- | 3-trimethylsilyl-phenyl | cyclopropyl | oil |
| 99 | 5- | 2-pyridyl | isopropyl | oil |
| 100 | 5- | 2-pyridyl | trifluoromethyl | m.p. 110° C. |
| 101 | 5- | 4-fluoro-3-trifluoromethyl-phenyl | cyclopropyl | oil |

TABLE 3-continued $$R^4R^5C=NOCH_2-\underset{\underset{7}{6}}{\overset{4}{\underset{S}{\bigcirc}}}\overset{CH_3OHC}{\underset{}{\diagdown}}C-COOCH_3$$

| Example | Position of R⁴R⁵C=NOCH₂— | | | Physical data |
|---|---|---|---|---|
| 102 | 5- | 3-fluoro-5-trifluoro-methyl-phenyl | cyclopropyl | oil |
| 103 | 5- | 3-fluorophenyl | cyclopropyl | oil |
| 104 | 5- | cyclopropyl | methyl | [E] isomers: m.p. 112–114° C. [Z] isomers: oil |
| 105 | 5- | 3-bromophenyl | cyclopropyl | oil |
| 106 | 5- | n-propyl | methyl | oil |
| 107 | 5- | ethyl | methyl | oil |
| 108 | 5- | isobutyl | methyl | oil |
| 109 | 5- | cyclohexyl | methyl | oil |
| 110 | 5- | benzyl | methyl | oil |
| 111 | 5- | α,α,α-trifluoro-m-tolyl | hydrogen | m.p. 117° C. |
| 112 | 5- | α,α,α-trifluoro-m-tolyl | isopropyl | oil |
| 113 | 5- | 2-methylthio-5-trifluoromethyl-phenyl | methyl | oil |
| 114 | 5- | 4-fluorophenyl | methyl | m.p. 138–140° C. |
| 115 | 5- | 3-fluorophenyl | n-propyl | oil |
| 116 | 5- | 3,4-dichlorophenyl | hydrogen | m.p. 157–159° C. |
| 117 | 5- | 2-pyridyl | hydrogen | m.p. 82° C. |
| 118 | 5- | 3-fluorophenyl | hydrogen | m.p. 112–114° C. |
| 119 | 5- | p-tolyl | methyl | m.p. 116–117° C. |
| 120 | 5- | 4-methoxy-3-methyl-thiomethyl-phenyl | methyl | m.p. 123–124° C. |
| 121 | 5- | 3-ethylphenyl | methyl | oil |
| 122 | 5- | α,α,α-trifluoro-p-tolyl | hydrogen | m.p. 165–166° C. |
| 123 | 5- | 3-bromophenyl | methoxyphenyl | m.p. 116–117° C. |
| 124 | 5- | 4-iodophenyl | methyl | m.p. 144–145° C. |
| 125 | 5- | ethoxy | methyl | oil |
| 126 | 5- | phenyl | phenyl | m.p. 141–142° C. |
| 127 | 5- | benzoyl | methyl | m.p. 95–96° C. |
| 128 | 5- | 2-thiazolyl | hydrogen | m.p. 215–217° C. |
| 129 | 5- | 3-(3-methyl-2-butenyloxy)-phenyl | methyl | oil |
| 130 | 5- | 3-trimethylsilyl-phenyl | trifluoromethyl | oil |
| 131 | 5- | 2-thienyl | tert-butyl | m.p. 131° C. |
| 132 | 5- | 3-(α,α,α-trifluoro-m-tolyl-oxy)-phenyl | hydrogen | oil |
| 133 | 5- | 2-thiazolyl | n-propyl | m.p. 111–112° C. |
| 134 | 5- | 2-thienyl | n-propyl | oil |
| 135 | 5- | 5-(2,3-dihydro-benzofuranyl) | methyl | oil |
| 136 | 5- | 6-(1,4-benzo-dioxanyl) | methyl | oil |
| 137 | 5- | 2-thienyl | ethyl | m.p. 86–87° C. |
| 138 | 5- | 2,5-dimethyl-3-thienyl | methyl | m.p. 110–111° C. |
| 139 | 5- | 3-benzyloxyphenyl | methyl | oil |
| 140 | 5- | 2-thienyl | hydrogen | oil |
| 141 | 5- | 3-thienyl | hydrogen | oil |
| 142 | 5- | phenyl | methylthiomethyl | oil |
| 143 | 5- | phenyl | methoxymethyl | oil |
| 144 | 5- | 2,5-difluorophenyl | methyl | m.p. 123–124° C. |
| 145 | 5- | 3-chloro-4-fluoro-phenyl | methyl | m.p. 148–150° C. |
| 146 | 5- | p-(n-propyl)-phenyl | methyl | m.p. 99–100° C. |
| 147 | 5- | 4-fluoro-3-trifluoro-methyl-phenyl | isopropyl | oil |
| 148 | 5- | 4-fluoro-3-trifluoro-methyl-phenyl | methoxymethyl | oil |
| 149 | 5- | 3-bromophenyl | isopropyl | oil |
| 150 | 5- | 3-chlorophenyl | isopropyl | oil |
| 151 | 5- | 3-bromophenyl | n-propyl | oil |
| 152 | 5- | 3-chlorophenyl | n-propyl | oil |

TABLE 3-continued

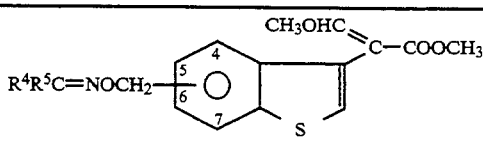

| Example | Position of $R^4R^5C=NOCH_2-$ | | | Physical data |
|---|---|---|---|---|
| 153 | 5- | 4-fluoro-3-trifluoro-methyl-phenyl | n-propyl | oil |

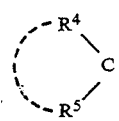

| | | | | |
|---|---|---|---|---|
| 154 | 5- | 3-methyl-5,6-dihydro-2H-1,4-thiazin-2-ylidene | | m.p. 158–159° C. |
| 155 | 5- | 3-ethyl-5,6-dihydro-2H-1,4-thiazin-2-ylidene | | m.p. 106° C. |
| 156 | 5- | 3-isopropyl-5,6-dihydro-2H-1,4-thiazin-2-ylidene | | m.p. 119–120° C. |
| 157 | 5- | 3-cyclopropyl-5,6-dihydro-2H-1,4-thiazin-2-ylidene | | m.p. 159–160° C. |
| 158 | 5- | 3-phenyl-5,6-dihydro-2H-1,4-thiazin-2-ylidene | | m.p. 129–130° C. |
| 159 | 5- | 2,4-dimethyl-2,4-dihydro-thiazol-5-ylidene | | m.p. 137–138° C. oil |
| 160 | 5- | 2-isopropyl-4-methyl-2,5-dihydro-thiazol-5-ylidene | | oil |
| 161 | 5- | 3-(4-chlorophenyl)-5,6-dihydro-2H-1,4-thiazin-2-ylidene | | m.p. 111–112° C. |
| 162 | 5- | 2-ethyl-2,4-dimethyl-2,5-dihydro-thiazol-5-ylidene | | m.p. 113–114° C. |
| 163 | 5- | 2,2-dimethyl-4-isopropyl-2,5-dihydro-thiazol-5-ylidene | | |
| 164 | 5- | 4,5,5-trimethyl-2,5-dihydro-thiazol-2-ylidene | | m.p. 145–147° C. oil |
| 165 | 5- | cyclopentylidene | | oil |
| 166 | 5- | 1H-indan-1-ylidene | | |
| 167 | 5- | cyclohexylidene | | oil |
| 168 | 5- | 9H-fluoren-9-ylidene | | m.p. 154° C. |
| | | $R^4$ | $R^5$ | |
| 169 | 5- | p-tolyl | trifluoromethyl | oil |
| 170 | 5- | 3-bromophenyl | trifluoromethyl | oil |
| 171 | 5- | 3-chlorophenyl | trifluoromethyl | oil |
| 172 | 5- | 2,4-dichlorophenyl | 2-fluorophenyl | oil |
| 173 | 5- | 5-(1,3-benzodioxola-nyl) | cyclopropyl | oil |
| 174 | 5- | 5-bromo-2-thienyl | methyl | oil |
| 175 | 5- | 5-methyl-2-furanyl | methyl | oil |
| 176 | 5- | 3-(α,α,α-trifluoro-m-tolyloxy)-phenyl | methyl | oil |
| 177 | 5- | 2-chlorophenyl | methyl | oil |
| 178 | 5- | 4-bromophenyl | methyl | m.p. 132–133° C. |
| 179 | 5- | 3-phenoxyphenyl | hydrogen | oil |
| 180 | 5- | p-tolyl | hydrogen | m.p. 128–129° C. |
| 181 | 5- | 4-bromophenyl | ethyl | oil |
| 182 | 5- | 3,4-dimethoxyphenyl | methyl | oil |
| 183 | 5- | 4-ethylphenyl | hydrogen | oil |
| 184 | 5- | 2,4-dimethoxyphenyl | methyl | oil |

EXAMPLE 185

A solution of 10 g of dimethyl {3-(α-methoxycarbonyl-β-methoxyvinyl)-5-benzo[b]thienyl}methylphosphonate in 20 ml of tetrahydrofuran is added dropwise to a suspension of 1.3 g of sodium hydride in 30 ml of tetrahydrofuran. 3 ml of benzaldehyde are then added, and the reaction mixture is stirred for 2 hours at room temperature. It is subsequently concentrated, and water is added, and the mixture is extracted with ethyl acetate. The organic phase is dried over anhydrous sodium sulfate and concentrated under reduced pressure, and the residue is then purified by chromatography on silica gel using methylene chloride/n-hexane (1:1). Recrystallization from methylene chloride/ethyl acetate/n-hexane gives methyl α-(5-styryl-3-benzo[b]thienyl)-β-methoxyacrylate as colourless crystals, m.p. 180°–181 ° C.

EXAMPLES 186–188

Analogously to the process described in Example 185, dimethyl {3-(α-methoxycarbonyl-β-methylvinyl)-5-benzo[b]thienyl}methylphosphonate is reacted with the aldehyde in question, of the formula V, to prepare the compounds of the formula I listed in Table 4 below:

TABLE 4

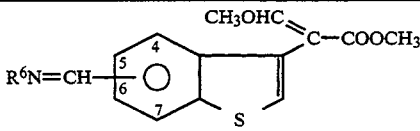

| Example | Position of R¹CH=CH— | R¹ | Physical data |
|---|---|---|---|
| 186 | 5- | α,α,α-tri-fluoro-m-tolyl | m.p. 145–146° C. |
| 187 | 5- | 3-thienyl | m.p. 214–215° C. |
| 188 | 5- | 2-pyridyl | m.p. 126–127° C. |

TABLE 5

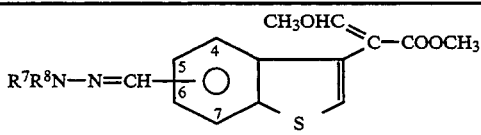

| Example | Position of R⁶CH=CH— | R⁶ | Physical data |
|---|---|---|---|
| 190 | 5- | methoxy | m.p. 148–149° C. |
| 191 | 5- | ethoxy | m.p. 98–99° C. |
| 192 | 5- | allyloxy | m.p. 83–84° C. |
| 193 | 5- | benzyloxy | m.p. 142–143° C. |
| 194 | 5- | 4-chlorobenzyloxy | m.p. 134–135° C. |
| 195 | 5- | 3,4-dichloro-benzyloxy | m.p. 142–143° C. |

TABLE 6

| Example | Position of R⁷R⁸N—N=CH— | R⁷R⁸N | Physical data |
|---|---|---|---|
| 196 | 5- | dimethylamino | m.p. 172–173° C. |
| 197 | 5- | phenylamino | m.p. 229–233° C. (with decomposition) |
| 198 | 5- | p-tolylsulfonylamino | m.p. 162–167° C. (with decomposition) |
| 199 | 5- | 6-chloro-2-pyridylamino | m.p. 195–196° C. |
| 200 | 5- | 3-chloro-5-trifluoromethyl-2-pyridylamino | m.p. 217–218° C. |
| 201 | 5- | 2-pyridylamino | m.p. 221–222° C. |
| 202 | 5- | 7-chloro-4-quinolinylamino | m.p. 159–161° C. |
| 203 | 5- | 4,6-dimethyl-2-pyrimidinyl-amino | m.p. 161° C. |
| 204 | 5- | 6-methyl-4-trifluoromethyl-2-pyridylamino | m.p. 186–188° C. |
| 205 | 5- | (methyl)6-methyl-4-trifluoro-methyl-2-pyridyl)amino | m.p. 225–226° C. |

EXAMPLE 189

A mixture of 0.9 g of methyl α-(5-formyl-3-benzo[b]-thienyl)-β-methoxyacrylate, 0.3 ml of aniline and a catalytic amount of p-toluenesulfonic acid in 30 ml of ethanol is refluxed for 1 hour. The mixture is then concentrated under reduced pressure, saturated sodium hydrogencarbonate solution is added, and the mixture is extracted three times using ethyl acetate. The combined organic phases are dried over anhydrous sodium sulfate and then concentrated. This gives methyl α-(5-phenylimino-3-benzo[b]-thienyl)-β-methoxyacrylate as yellow crystals, m.p. 152° C.

EXAMPLES 190–205

Analogously to the process described in Example 189, methyl α-(5-formyl-3-benzo[b]thienyl)-β-methoxyacrylate is reacted with the amine or hydroxylamine in question, of the formula VII, or with hydrazine, of the formula VIII, to prepare the compounds of the formula I listed in Tables 5 and 6 below.

II. Preparation of the starting materials of the formula IV

EXAMPLE 206

A mixture of 20 g of methyl α-(5-bromomethyl-3-benzo[b]thienyl)-β-methoxyacrylate (see Example 11), 7.1 ml of the trimethyl ester of phosphorous acid and 3.5 ml of toluene is refluxed for 2 hours. The mixture is then concentrated under reduced pressure, and the oil which remains is purified by chromatography on silica gel, namely first using ethyl acetate and subsequently using ethyl acetate/methanol (9:1 ). This procedure gives dimethyl {3-(α-methoxycarbonyl)-β-methoxyvinyl)-5-benzo[b]thienyl}methylphosphonate as a yellow oil.

III. Preparation of the starting materials of the formula VI

EXAMPLE 207

A mixture of 2 g of methyl α-(5-bromomethyl-3-benzo[b]thienyl)-13-methoxyacrylate (see Example 11), 16 ml of dimethyl sulfoxide and 0.5 g of sodium hydrogencarbonate is heated at 85° C. for 2.5 hours. Water is subsequently added, and the mixture is extracted using ethyl acetate. The organic phase is dried over anhydrous sodium sulfate and concentrated under reduced pressure, and the residue is then purified by chromatography on silica gel using diethyl ether/n-hexane (2:1). Recrystallization from methylene chloride/n-hexane gives methyl α-(5-formyl-3-benzo[b]thienyl)-β-methoxyacrylate as colourless crystals, m.p. 134°–135° C.

IV. Formulation examples

EXAMPLE 208

An emulsifiable concentrate consists of the following:

|  | g/liter |
|---|---|
| Active substance (compound according to the invention) | 100 |
| Nonylphenol (10)ethoxylate (non-ionic emulsifier) | 50 |
| Calcium dodecylbenzenesulfonate (anionic emulsifier) | 25 |
| N-methyl-2-pyrrolidone (solubilizer) | 200 |
| Alkylbenzene mixture (solvent) | to 1 l |

The active substance and the emulsifiers are dissolved in the solvent and in the solubilizer. A ready-for-use spray liquor of any desired concentration can be prepared by emulsifying this concentrate in water.

EXAMPLE 209

A wettable powder consists of the following:

|  | Percent per weight |
|---|---|
| Active substance (compound according to the invention | 25.0 |
| Silica (hydrated; carrier) | 20.0 |
| Sodium lauryl sulfate (wetting agent) | 2.0 |
| Sodium lignosulfonate (dispersant) | 4.0 |
| Kaolin (carrier) | 49.0 |

The components are mixed with each other, and the mixture is ground finely in a suitable mill. Dispersion of the mixture in water gives a suspension which is suitable as a ready-for-use spray liquor.

What is claimed is:

1. A compound of the formula

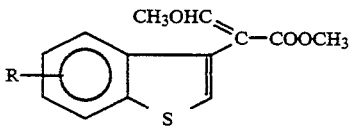

in which

R is halogen, $C_{1-4}$haloalkyl, $C_{1-4}$alkoxy-$C_{1-4}$alkyl, phenyl-$C_{1-4}$ alkoxy-$C_{1-4}$alkyl, phenoxy-$C_{1-4}$alkyl, phenylthio-$C_{1-4}$alkyl, $C_{2-5}$alkanoyloxy-$C_{1-4}$alkyl, optionally $C_{1-4}$alkyl-substituted $C_{3-6}$cycloalkyl-carbonyloxy-$C_{1-4}$alkyl, benzoyl-$C_{1-4}$-alkyl, phenyl-$C_{2-5}$alkanoyloxy-$C_{1-4}$alkyl, $C_{1-4}$alkoxy, phenoxy or one of the groups (a) to (e)

| $R^1CH=CH$ | (a) |
| $R^2R^3NCH_2$ | (b) |
| $R^4R^5C=NOCH_2$ | (c) |
| $R^6N=CH$ | (d) |
| $R^7R^8N-N=CH$ | (e), |

$R^1$ is phenyl,
$R^2$ and $R^3$ independently of one another are hydrogen, $C_{1-4}$alkyl, phenyl-$C_{1-4}$alkyl or phenyl,
or $R^2$ and $R^3$ together with the nitrogen atom to which they are bonded form a 5- or 6-membered ring which may contain an oxygen or sulfur atom,
$R^4$ and $R^5$ independently of one another are hydrogen, $C_{1-4}$alkyl, $C_{1-4}$haloalkyl, $C_{1-4}$alkoxy-$C_{1-4}$alkyl, $C_{1-4}$alkylthio-$C_{1-4}$alkyl, phenyl-$C_{1-4}$alkyl, $C_{3-6}$cycloalkyl, phenyl, $C_{1-4}$alkoxy or benzoyl,
or
$R^4$ and $R^5$ together with the carbon atom to which they are bonded form (1) a 5- or 6-membered heterocyclic ring having up to two hereto atoms selected from N and S or (2) a 5- or 6- membered carbocyclic ring to which one or two benzene rings may be fused,
$R^6$ is phenyl, $C_{1-4}$alkoxy, phenyl-$C_{1-4}$alkoxy or $C_{3\ or\ 4}$alkenyloxy,
and
$R^7$ and $R^8$ independently of one another are hydrogen, $C_{1-4}$alkyl, phenyl, or phenylsulfonyl;
the foregoing phenyl substituents being unsubstituted or substituted by a substituent selected from the group consisting of halogen, $C_{1-4}$alkyl, $C_{1-4}$haloalkyl, $C_{1-4}$alkylthio-$C_{1-4}$alkyl, $C_{1-4}$alkoxy, $C_{1-4}$haloalkoxy, phenyl-$C_{1-4}$alkoxy, $C_{1-4}$alkenyloxy, phenoxy, $C_{1-4}$alkylthio, $C_{1-4}$cycloalkyl-$C_{1-4}$alkylthio, nitro and tri($C_{1-4}$alkyl)silyl.

2. A compound as claimed in claim 1, in which the substituent R is in the 5-position of the benzo[b]thiophene ring.

3. A compound as claimed in claim 22 in which halogen, $C_{1-4}$haloalkyl, $C_{1-4}$alkoxy-$C_{1-4}$alkyl, phenoxy-$C_{1-4}$alkyl, phenylthio-$C_{1-4}$alkyl, $C_{1-4}$alkoxy, phenoxy or one of the groups (a) to (d), $R^1$, $R^2$ and $R^3$ are as defined in claim 2, and $R^4$ and $R^5$ independently of one another are hydrogen, $C_{1-4}$alkyl, $C_{1-4}$haloalkyl, $C_{1-4}$alkoxy-$C_{1-4}$alkyl, $C_{3-6}$cycloalkyl or phenyl and $R^6$ is phenyl.

4. A compound as claimed in claim 3, selected from amongst

Methyl α-(5-(α-methyl-m-trifluoromethylbenzylideneaminooxymethyl)-3-benzo[b]thienyl}-β-methoxyacrylate, methyl α-{5-(α-[n-propyl]-benzylideneaminooxymethyl)-3-benzo[b]thienyl}-g-methoxyacrylate, methyl α-{5-(α-cyclopropyl-4-chlorobenzylideneaminooxymethyl)-3-benzo[b]thienyl}-β-methoxyacrylate, methyl α-{5-methoxy-3-benzo[b]thienyl}-β-methoxyacrylate, methyl α-{5-ethoxy-3-benzo[b]thienyl}-13-methoxyacrylate, methyl α-{5-[(α-phenylethyl)methylaminomethyl]-3-benzo[b]thienyl}-β-methoxyacrylate, methyl α-{5-(dicyclopropylmethylideneaminooxymethyl)-3-benzo[b]thienyl}-β-methoxyacrylate, methyl α-{5-(α-cyclopropyl-m-trifluoromethylbenzylideneaminooxymethyl)-3-benzo[b]thienyl}-β-methoxyacrylate.

5. A compound as claimed in claim 1, selected from amongst:

methyl α-{5-(α-cyclopropylbenzylideneaminooxymethyl)-3-benzo[b]thienyl}-β-methoxyacrylate, methyl α-{5-[g-methyl-α-(2-pyridyl)-propylideneaminooxymethyl]-3-benzo[b]thienyl}-β-methoxyacrylate and methyl α-{5-(2-isopropyl-4-methyl-2,5-dihydrothiazol-5-ylideneamino oxymethyl)-3-benzo[b]thienyl}-β-methoxyacrylate.

6. A compound as claimed in claim 3, in which the substituent R is in the 5-position of the benzo[b]thiophene ring.

7. The compound methyl α-{5-(α-methyl-m-[α,α,α-trifluoro-m-tolyloxy]-benzylideneaminooxymethyl)-3-benzo[b]thienyl}-β-methoxyacrylate.

8. A fungicidal composition which contains an effective amount of a compound as defined in claim 1 and formulation auxiliaries.

9. A fungicidal composition as claimed in 8, which contains an effective amount of a compound selected from the group consisting of:

methyl α-{5-(α-methyl-m-trifluoromethylbenzylideneaminooxymethyl)-3-benzo[b]thienyl}-β-methoxyacrylate, methyl α-{5-(α-[n-propyl]-benzylideneaminooxymethyl]-3-benzo[b]thienyl}-β-methoxyacrylate, methyl α-{5-(α-cyclopropyl-4-chlorobenzylideneaminooxymethyl)-3-benzo[b]thienyl}-β-methoxyacrylate, methyl α-{5-methoxy-3-benzo[b]thienyl}-β-methoxyacrylate, methyl α-{5-ethoxy-3-benzo[b]thienyl}-β-methoxyacrylate, methyl α-{5-[(α-phenylethyl)methylaminomethyl]-3-benzo[b]thienyl}-β-methoxyacrylate, methyl α-{5-(dicyclopropylmethylideneaminooxymethyl)-3-benzo[b]thienyl}-β-methoxyacrylate, methyl α-{5-(α-cyclopropyl-m-trifluoromethylbenzylideneaminooxymethyl)-3-benzo[b]thienyl}-β-methoxyacrylate, and also formulation auxiliaries.

10. A fungicidal composition as claimed in claim 8, which contains an effective amount of a compound selected from the group consisting of:

methyl α-{5-(α-cyclopropylbenzylideneaminooxymethyl)-3-benzo[b]thienyl}-β-methoxyacrylate, methyl α-{5-(2-isopropyl-4-methyl-2,5-dihydrothiazol-5-ylidene aminooxymethyl)-3-benzo[b]thienyl}-β-methoxyacrylate, and also formulation auxiliaries.

11. A method of controlling fungi in agriculture and in horticulture, which comprises treating the goods to be protected with an effective amount of a compound as claimed in claim 1.

12. A method of controlling fungi in agriculture and in horticulture, which comprises treating the goods to be protected with an effective amount of a compound as claimed in claim 1.

13. A method according to claim 11 wherein the compound is a compound wherein the substituent R is in the 5-position of the benzo[b]thiophene ring.

14. A method according to claim 11 wherein the compound is a compound selected from the group consisting of methyl α-{5-(α-cyclopropylbenzylideneaminooxymethyl)-3-benzo[b]thienyl}-β-methoxyacrylate, and methyl α-{5-(2-isopropyl-4-methyl-2,5-dihydrothiazol-5-ylideneamino oxymethyl)-3-benzo[b]thienyl}-β-methoxyacrylate.

15. A method for controlling fungi in agriculture or horticulture which comprises treating goods to be protected with a composition as defined in claim 10.

16. A method for controlling fungi in agriculture or horticulture which comprises treating goods to be protected with a composition as defined in claim 10.

17. A method for controlling fungi in agriculture or horticulture which comprises treating goods to be protected with an effective amount of a compound as defined in claim 4.

18. A method for controlling fungi in agriculture or horticulture which comprises treating goods to be protected with an effective amount of a composition as defined in claim 9.

* * * * *

UNITED STATES PATENT AND TRADEMARK OFFICE
CERTIFICATE OF CORRECTION

PATENT NO. : 5,376,677
DATED : December 27, 1994
INVENTOR(S) : Stephan TRAH et al.

It is certified that error appears in the above-indentified patent and that said Letters Patent is hereby corrected as shown below:

On the cover page:
"UNITED STATES PATENT [19]" change "Trah" to read "Trah et al."

On the cover page of the patent, the left hand column, correct Section [75] Inventor: to read "Stephen Trah, Freiburg im Breisgau, Germany; Francois Gantz, Rixhelm, France".

Signed and Sealed this

Eighteenth Day of April, 1995

Attest:

BRUCE LEHMAN

Attesting Officer

Commissioner of Patents and Trademarks